US006753782B2

United States Patent
Power

(10) Patent No.: US 6,753,782 B2
(45) Date of Patent: Jun. 22, 2004

(54) SYSTEM FOR MONITORING PATIENTS WITH ALZHEIMER'S DISEASE OR RELATED DEMENTIA

(75) Inventor: Michael W. Power, Hunter River (CA)

(73) Assignee: Vitrak Wireless Inc., Halifax (CA)

( * ) Notice: Subject to any disclaimer, the term of this patent is extended or adjusted under 35 U.S.C. 154(b) by 38 days.

(21) Appl. No.: 09/985,075

(22) Filed: Nov. 1, 2001

(65) Prior Publication Data

US 2002/0060630 A1 May 23, 2002

(30) Foreign Application Priority Data

Jan. 11, 2000 (CA) .............................................. 2324967

(51) Int. Cl.⁷ .............................................. G08B 23/00
(52) U.S. Cl. .............................. 340/573.4; 340/572.8; 340/539; 340/571; 340/552
(58) Field of Search ........................... 340/573.4, 572.8, 340/539, 571, 552

(56) References Cited

U.S. PATENT DOCUMENTS

| | | | | |
|---|---|---|---|---|
| 4,952,928 A | * | 8/1990 | Carroll et al. ......... | 340/825.54 |
| 5,119,072 A | * | 6/1992 | Hemingway ................ | 340/573 |
| 5,335,664 A | * | 8/1994 | Nagashima ................. | 128/696 |
| 5,440,290 A | * | 8/1995 | McCullough et al. ....... | 340/552 |
| 5,485,163 A | * | 1/1996 | Singer et al. ................ | 342/457 |
| 5,515,419 A | * | 5/1996 | Sheffer ......................... | 379/58 |
| 5,652,570 A | * | 7/1997 | Lepkofker ................... | 340/573 |
| 5,714,932 A | * | 2/1998 | Castellon et al. ........... | 340/539 |
| 5,771,002 A | * | 6/1998 | Creek et al. ................. | 340/539 |
| 5,809,243 A | * | 9/1998 | Rostoker et al. ........ | 395/200.47 |
| 5,905,461 A | * | 5/1999 | Neher .......................... | 342/357 |
| 6,104,295 A | * | 8/2000 | Gaisser et al. ........... | 340/573.4 |

* cited by examiner

Primary Examiner—Daniel J. Wu
Assistant Examiner—Tai T. Nguyen
(74) Attorney, Agent, or Firm—Smart & Biggar

(57) ABSTRACT

A system is provided for monitoring the behavior, behavior patterns and movements of patients with Alzheimer's, related dementia and a range of other diseases, disorders and injuries including childhood autism, attention deficit disorder (ADD), schizophrenia, severe clinical depression, brain injury, and conditions such as recovery from hip replacement surgery. The monitoring system comprises: a transmitter worn by the patient which emits an identification signal; a detector placed at a hazard or a at a location to be monitored, the detector capable of determining the distance of the patient from the detector and determining the occurrence of an incident when the distance falls below a predetermined threshold; a receiving unit for receiving the information transmitted by the detector; and database means for accumulating information received by the receiving unit. The purpose of the system is to safeguard patients from injury and to generate, accumulate and analyze data and information about these diseases, conditions and disorders.

43 Claims, 6 Drawing Sheets

SYSTEM FOR MONITORING PATIENTS WITH ALZHEIMER'S DISEASE OR RELATED DEMENTIA

FIELD OF THE INVENTION

The present invention relates to a system for monitoring persons under care, such as patients with Alzheimer's and related dementia, as well as those suffering from a range of other medical conditions, disorders and diseases (e.g. severe clinical depression, schizophrenia, childhood autism, brain injury, attention deficit disorder (ADD) and conditions such as recovery from hip replacement surgery), and in particular, tracking their movements relative to certain predetermined locations and hazards.

BACKGROUND OF THE INVENTION

Monitoring systems for tracking or controlling the movement of persons such as children, patients and prisoners are known.

For example, U.S. Pat. No. 5,751,214 granted to Cowley et al. on May 12, 1998 describes a device for monitoring the movement of a patient. Multiple sensors are used to monitor the patient's movement and these provide signals to a unit capable of activating an alarm to indicate the movement of the patient beyond a prescribed limit or to indicate other conditions. Information received from the sensors are stored and then transferred to a remote computer for evaluating a patient's care. A disadvantage of Cowley et al. is that their device is designed to restrict the patient's movement.

Another example is U.S. Pat. No. 6,054,928 granted to Lemelson et al. on Apr. 25, 2000. Lemelson et al. teach a system wherein data relating to a prisoner is obtained by a sensor/processor unit worn by the prisoner to track the location of the prisoner and to monitor physical conditions of the prisoner. The sensor/processor unit communicates with a control center via radio links or through "home base" via a telephone link. A control center has an associated data storage and is used to collect the data and compare it with authorized activities and to learn about the behavior of the prisoner.

Lemelson et al. use GPS technology which can be more expensive than wireless radio signal technology. In addition, Lemelson et al. use a "hard wired" transmission process and cannot function as a wireless system. The technology of Lemelson et al. seeks to restrict and contain the prisoner.

In both Lemelson et al. Cowley et al. the controls are not in place for benefit of the clients, patients and prisoners. Instead, the controls are in place for administrators caregivers, guards and institutions.

These examples of prior art are also limited in overall capacity. Specifically, they cannot collect and analyze data in a manner that will measurably impact upon and advance prevention strategies, mitigate harm, and facilitate the identification of behavioral and medical treatment interventions for diseases such as Alzheimer's and related dementia.

By contrast, the present invention focuses on positive enabling reinforcers; enables the collection and analysis of data and information of a nature and scope never previously available; and enables researchers to systematically identify and assess unique approaches, interventions and treatments both behavioral and medical to prevent or mitigate the effects of selected degenerative disorders and diseases. Being able to anticipate both adaptive and non-adaptive behaviors and patterns of behaviors among such patients could potentially lead to improved treatment interventions, better overall patient management and enhancement in the quality of patients' lives, Alzheimer's disease was first discovered and described by a German psychiatrist (Aldis Alzheimer) around the beginning of the $19^{th}$ century. Alzheimer's disease is a degenerative disease of the brain characterized by progressive loss of mental and physical faculties. Some progress has been made in our ability to detect and diagnose Alzheimer's disease but progress has been minimal.

In the mid-1960s the only way to confirm absolutely that a patient was afflicted with Alzheimer's disease was to dissect the patient's brain after death. Nearly forty years later autopsy is still the only way to confirm the diagnosis. There is no cure in sight and medications which show real promise are unlikely to be available for widespread use and distribution until approximately 2007.

In the United States alone, it is believed there are now 4,000,000 people with Alzheimer's disease. The incidence of the disease is on the increase and it is estimated that in the United States there will be approximately 14,000,000 or more men and women with Alzheimer's disease before the middle of this century. This is a potentially catastrophic world wide problem. Unfortunately, it will be further exacerbated by markedly increased life expectancy, primarily attributable to advances in medical science.

Scientists and medical practitioners are working hard to find potential solutions through medical research and experimentation with medication. Data, derived or collected through clinical observation and the use of available technology, are urgently required to provide insights into the factors and variables which impact upon or determine differential rates of degeneration and progression of this deadly disease.

The present invention will facilitate the easy and systematic collection and analysis of massive amounts of objective and verifiable data. Such data are likely to reveal knowledge about Alzheimer's disease and related dementia and their concomitants. Additionally, the invention will help to safeguard the lives of people with Alzheimer's disease by preventing or substantially diminishing accidents, injuries and death in all institutional and private home settings where the invention is used.

SUMMARY OF THE INVENTION

Accordingly, it is an object of the present invention to overcome or mitigate the limitations present in conventional monitoring systems. It is another object of the present invention to collect objective data about patients' movements, behavior and patterns of behavior. A further object is to use this data to allow researchers to discover unique interventions and treatments which will enhance the quality of patients' lives, diminish stress among families and potentially reduce the cost of institutional and private home care. A still further object is to safeguard the lives of patients and to prevent accidents.

The present invention thus seeks not only to identify signs and signals of degeneration but also to diminish controls and improve patients' functioning. A result is that patients can be more effectively monitored on a day-to-day basis.

Accordingly, the invention provides a system for monitoring a person under care comprising: a transmitter worn by the person for emitting an identification signal; one or more detectors placed at or near a hazard or at or near a location to be monitored, the detector or detectors being capable of detecting the distance of the person from a detector and transmitting such information; and, in the case of a detector at or near a hazard, determining that an incident has occurred when the person's distance from the detector falls below a predetermined threshold and then transmitting information about the incident a receiving unit for receiving the information transmitted by the detector or detectors; and database means for accumulating and amalgamating information received by the receiving unit.

The term "person under care" is intended to include patients suffering from a medical condition, such as dementia, including Alzheimer's disease, clinical depression or schizophrenia as well as other persons requiring care or monitoring such as a child, mentally challenged person, elderly or infirm person or a behaviorally challenged person. Typical hazards near which the detectors may be placed include an appliance, machine, vehicle, staircase, or swimming pool. Other locations which can be monitored include a doorway, window, gate, home office, or a border of a property.

It is anticipated that the data accumulated in the database by many patients will, over time, accelerate and enhance the collection and analysis of potentially vital data. Such information may be useful in: conducting clinical trials; improving prescribing practices; monitoring the impact of medication; facilitating observations of side effects; determining more effective dosages of medication; and assisting caregivers in making informed decisions about the best and safest locations for patients. The data may also be used to develop or discover theoretical models, standards and characteristic features of various stages of degenerative disorders. There is currently a need to facilitate the discovery and development of unique programs, strategies and treatments for patients afflicted with Alzheimer's disease and related dementia.

Ultimately such advances may reduce cost for care and long-term management of patients with such disorders and reduce the high levels of stress and depression among patients with Alzheimer's disease and related disorders.

Advantages of the present invention include the ability to track patterns of movement of persons, such as patients; establish norms (related to movement, wandering and levels of agitation) for persons and patients of different ages, genders and other related variables; and substantially improve the accuracy and understanding of direct observations of patients' behaviors. The present invention will permit the systematic collection, compilation and analysis of data and information about movements, wandering behaviors and other patterns of behavior among patients with such diseases and disorders.

BRIEF DESCRIPTION OF THE DRAWINGS

Embodiments of the present invention will be further described with reference to the accompanying drawings, in which.

DETAILED DESCRIPTION OF THE PREFERRED EMBODIMENTS

Transmitter

Figure 1:
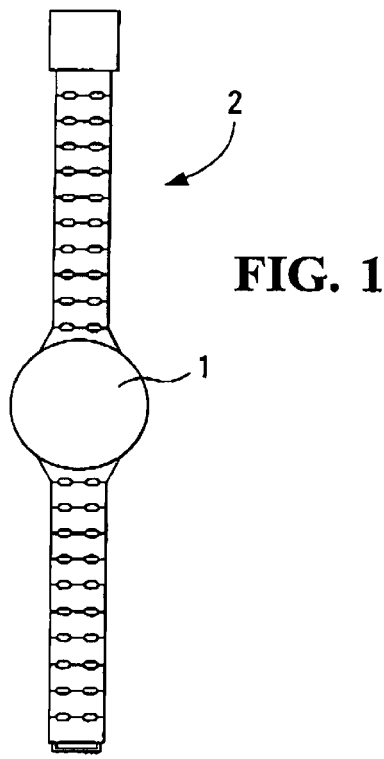
FIG. 1 illustrates a bracelet which contains an electronic monitoring tag according to a preferred embodiment of the present invention.
Figure 5:
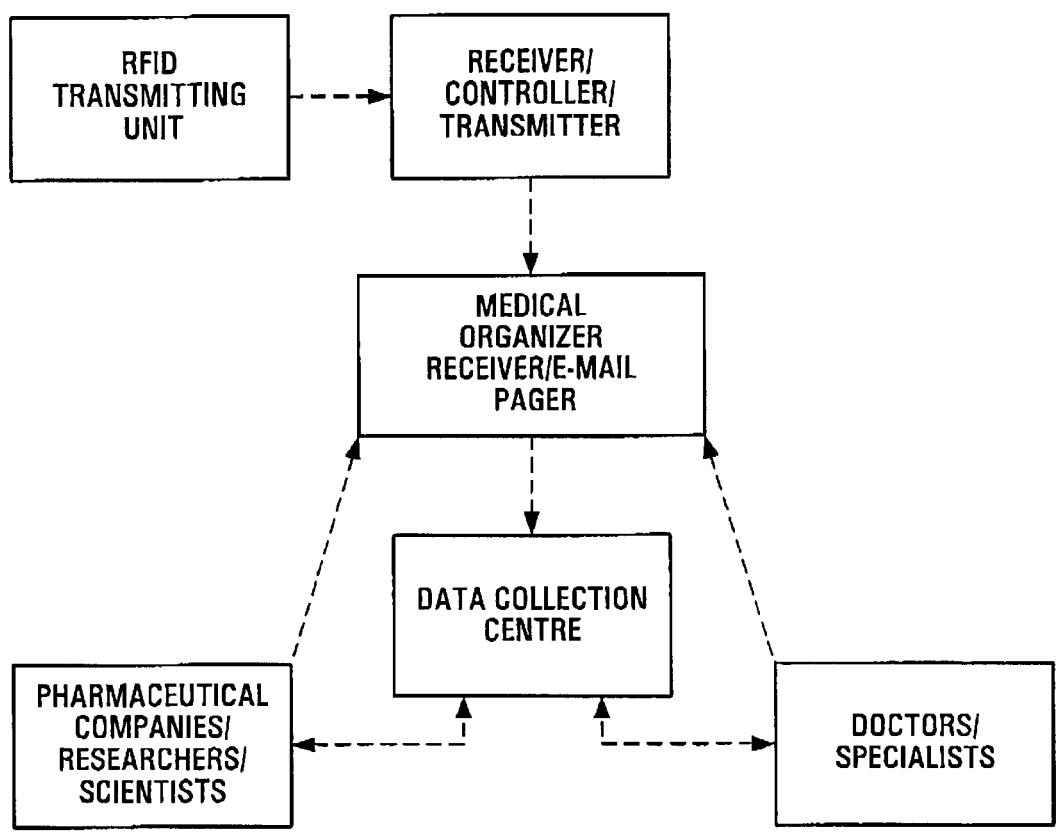
FIG. 5 is a block diagram illustrating the logical flow of the monitoring system.

Referring to FIGS. 1 and 5, according to a first embodiment of the present invention, a system includes a transmitter worn by a patient for emitting a patient information signal. The patient information signal includes an identifier unique to the patient. The transmitter, according to the present embodiment, is a radio frequency identification device (RFID) and is installed in an electronic monitoring tag 1 worn by the patient which, in this embodiment, is contained in a bracelet 2 somewhat analogous in appearance to a wristwatch. The electronic monitoring tag 1 contains internally thereof a controller, transmitter, antenna and a power source. Optionally, the tag includes means for monitoring the heart rate of the patient.

Thus, in most instances, the electronic monitoring tag 1 will be worn and displayed by the patient or client in the form of an arm band, broach, or as a watch-type bracelet 2 which is capable of performing all of the necessary functions of the transmitter. In situations where the patient resists wearing any of the above-noted devices, the tag can be disguised as a belt-buckle, shoe insert, or other similar device, or sewn or otherwise fixed in a clothing item, if desired in a concealed manner. According to a preferred embodiment of the invention, the electronic monitoring tag 1 is in the form of a bracelet 2; however, any number of devices can be employed and this should therefore not be taken in a limiting sense.

The bracelet may be regarded as a personal identification unit, which emits a burst of RF energy. Recorded within these bursts of energy are coded pieces of information that remain constant in the strength of their signal, as well as in the format of the information that they contain. The transmitter is a fixed frequency on/off keyed transmitter block that is driven on by the controller. The output radio frequency power of the device should be, but is not limited to −15 dBm±dB at a frequency of 418 MHZ±0.05 MHZ, although other frequencies such as phase modulation (PM), Amplitude modulation (AM), frequency modulation (FM), and Pulse position modulation may be used, as well as various combinations of modulation techniques, or other modulations.

Inside the bracelet there is a micro-controller that controls the function of the personal identification unit. It controls memory in which the transmission data is stored. The micro-controller itself could consist of microprocessor, logic array, logic devices, a state machine or other devices.

The transmitter/micro-controller are part of an incorporated circuit board that has a loop antenna attached as well. The type of antennae used will be determined by the configuration of the systems settings, and will be readily determined by those skilled in the art.

The electronic monitoring tag is also provided with means to detect removal from the patient whether by accident or intentionally. This is accomplished as follows. The electronic monitoring tag (or any personal identification unit) is powered with a battery which provides power to a continuity circuit which is incorporated in the system to allow for removal of the tag to be signalled in a variety of manners. Upon removal of the tag the continuity circuit is opened. This open circuit causes a signal to be transmitted in order to indicate the removal of the tag from the patient. Immediately upon removal of the tag, this will set off an audible alarm or an electronic signal. The decision as to whether the audible alarm or the electronic signal is used may be determined by the venue in which the patient is located. In other words, an audible alarm would normally suffice in a home environment because the alarm will be easily heard. For an institutional setting however, the electronic signal would probably be preferable since the size of the facility will likely limit the audible alarm from being effective. However, depending upon the configuration of the patient's living space and supervisory arrangements, a combination of both types of signalling is possible and may be preferred.

The patient, in this discussion, is assumed to be suffering from a degenerative condition, such as Alzheimer's disease, characterized by dementia. The patient is also assumed to be in a supervised environment such as in a hospital or a supervised home setting.

Detectors

As shown in FIG. 2, located within the supervised environment are detectors 3, 4, 5 and 6. Each detector contains a receiver demodulator, distance power measurement circuit, phase error measurement circuit, controller, receiving antenna and a power supply.

Figure 2A:
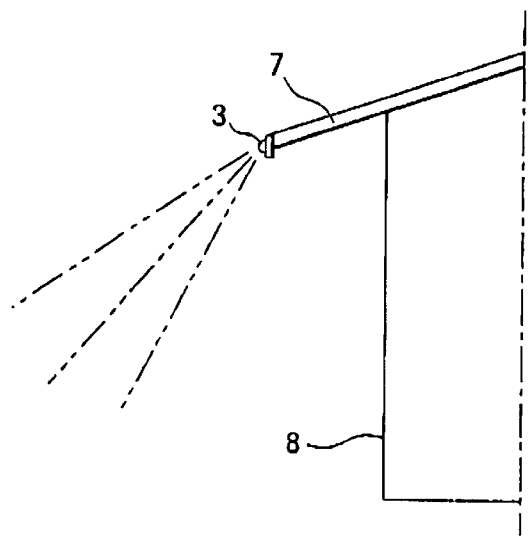
FIGS. 2A, 2B, 2C and 2D illustrate diagrammatically the detector receiving antennae in different locations for use with the electronic monitoring tag of FIG. 1.
Figure 2B:
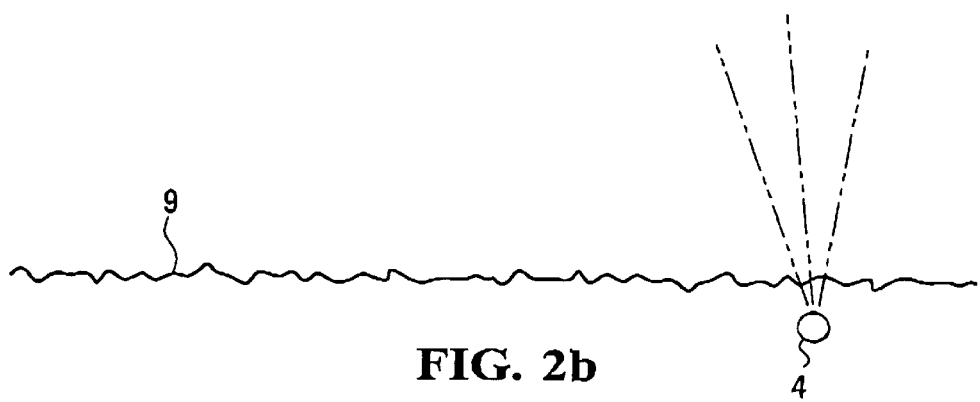
Figure 2C:
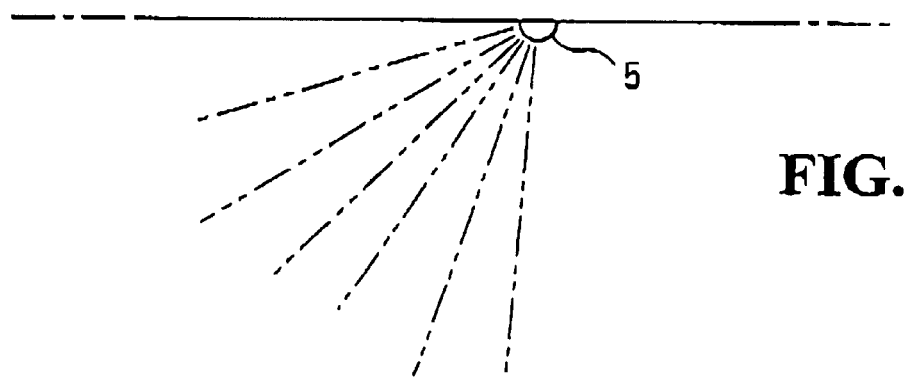
Figure 2D:
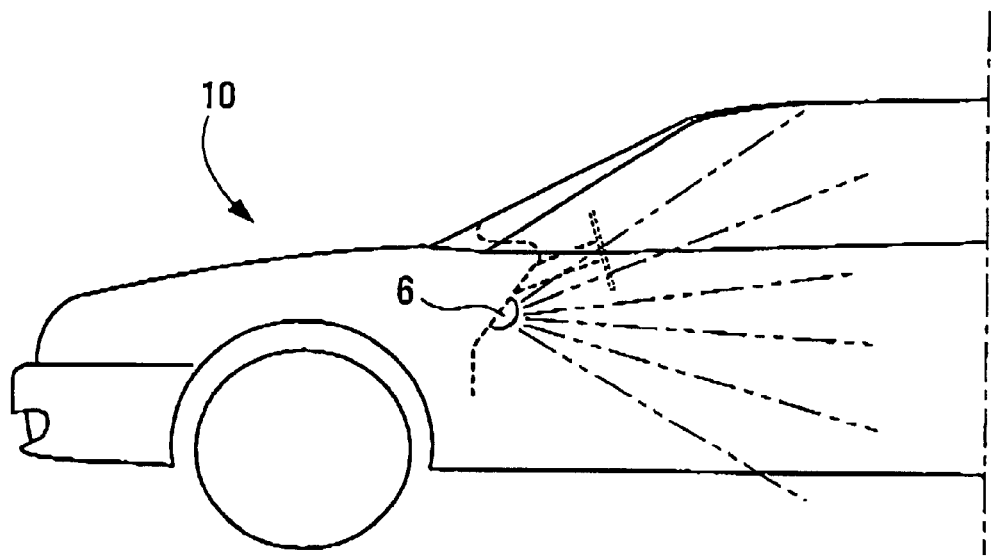

The detectors 3 to 6 are placed at strategic locations such as doorways, stairways and exits; and proximal or juxtaposed to hazards such as stoves and automobiles accessible to the patient. For example, referring to FIGS. 2A to 2D, the detectors 3, 4, 5, 6 can be installed in multiple locations in order to provide adequate monitoring. FIG. 2A illustrates an example where a detector 3 having a directional antenna is installed on the roof 7 of a building 8 such as a house. FIG. 2B illustrates an example where the antenna of a detector 4 is placed below a ground surface 9. FIG. 2C illustrates an example where a directional antenna of a detector 5 is placed in a doorway. FIG. 2D illustrates an example where a directional detector 6 is placed in an automobile 10 to detect the presence of the patient.

The detector detects the proximity of the patient to the detector based on the strength of reception of the signal from the transmitter. As the patient approaches a detector, the strength of the signal received from the transmitter increases. Conversely, as the patient withdraws from a detector, the strength of the signal received by the detector decreases. In addition, the antenna used in the detector can be directional or rotating. If the detector is rotating then it can be used to determine the position and direction of movement of the patient as described below.

Thus, the antenna is the receiver of the system and picks up the bursts of RF energy and relays the signal to a receiver demodulator within the receiver itself. The selection of antenna will depend on various options/parameters pertinent to a given context. A variety of configurations for antenna maybe chosen, including loop antenna, directional antenna and switched antenna array. The suitability of antennae will be apparent to those skilled in the art, and can directly depend on operating frequency. Depending on the distance from the receiver the antennae could be outfitted with a repeater, or could be directly wired to the receiver.

Within the detector is a receiver demodulator which demodulates the energy signal received by the detectors (antenna), the demodulated signal is passed on to a power measurement circuit which will in turn determine the distance of the identification unit, i.e. the transmitter. The controller is then provided with the distance measurement between the antenna (detector), and the transmitter. The controller includes a numerous range of detection thresholds that are adjustable by the system installer to account for the installation of antennae in various locations throughout the containment area. Included within the receiver may be a microprocessor/controller with memory, transmitter block driven by the controller, notification device, relay switch multiple antennae for receiving and one for transmitting information over the Internet. The receiver transmitter translates the RF signal, the patient location, how far they are from a hazard, whether the hazard is electronic in nature. If the incident is at an electrical/electronic appliance and the threshold has been exceeded, the controller may activate a relay switch, which deactivates the electrical appliance. Once all the information is processed in real time it may be sent via wireless communication to the Medical Organizer.

Controller

The information gathered by the detectors is transmitted to a controller for processing. Information received by the controller includes the patient's identifier, an identifier for the detector (such as a serial number), the received signal strength, and heart rate. In addition, if a more refined tracking is required, rotating detectors can be used to provide the information necessary to allow the controller to determine the patient's exact location, direction of movement and rate of movement.

Figure 8:
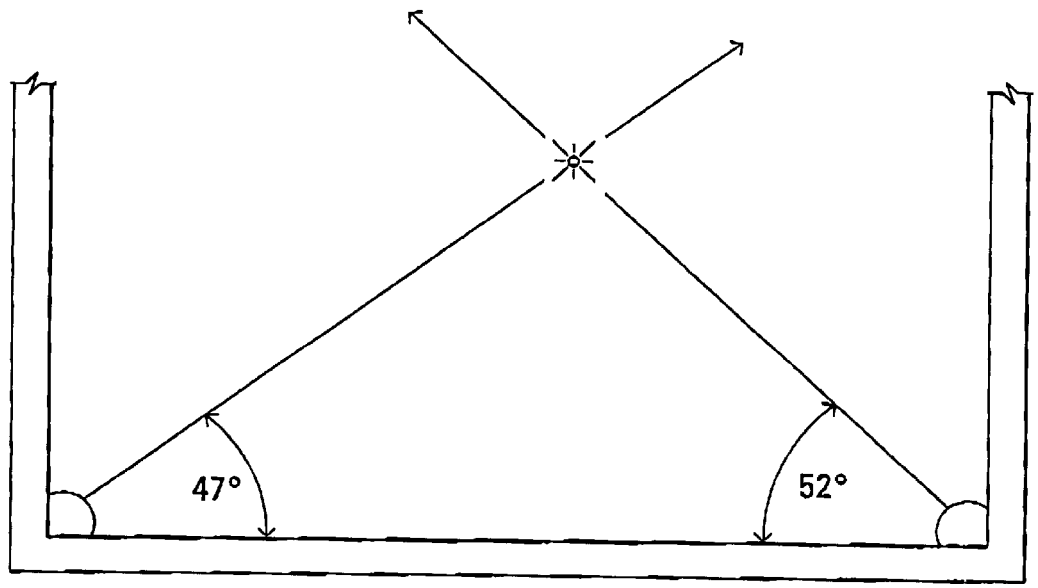
FIG. 8 illustrates diagrammatically the intersection of two antennae.

Referring to FIG. 8, a rotating antenna detecting a signal will receive that signal at different strengths as the antenna rotates. Assume that at the beginning of rotation the transmitter is not directly in the "line of sight" of the antenna. Then the strength of the signal $S_o$ is relatively weak when the angle of rotation is $q_1$. As the antenna rotates toward the location of the transmitter, the signal received increases in strength to a maximum $S_m$ which occurs when the antenna is oriented toward the transmitter at angle $q_m$. The system also notes the time t of this measurement. Then as the antenna continues to rotate to angle $q_2$, a subsequent signal received will have strength $S_2$, which is less than $S_m$.

In this way, by tracking the angle of rotation of the antenna and the strength of the signal, the position of the transmitter relative to the antenna can be determined. In particular, in the above example, the position of the patient is, using polar coordinates, $(S_m, q_m)$. Of course, the strength of the signal $S_m$ does not represent a physical distance but it is possible to convert signal strength to distance once the system has been calibrated.

Figure 9:
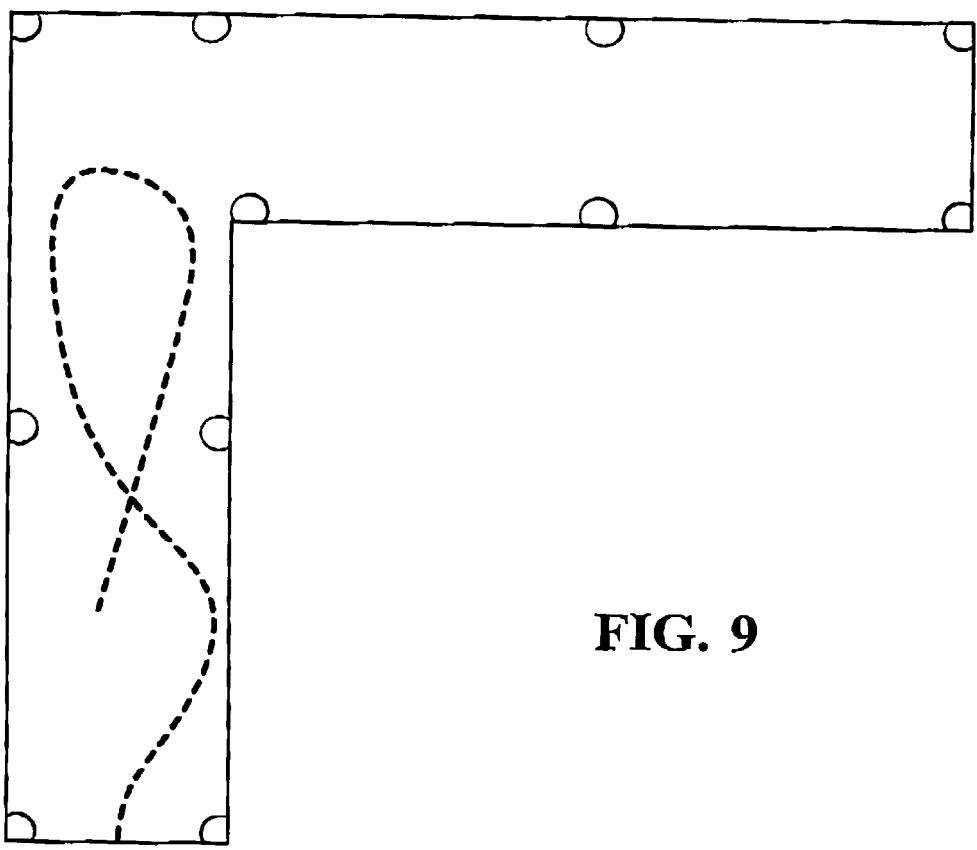
FIG. 9 is an example of the path of movement of a patient along the hallway of FIG. 6.

The present embodiment, however, prefers to use triangulation to determine a more accurate reading of the patients position as described below. When the detectors are mounted on the wall, for example, to determine movement, the detectors rotate in order to triangulate the movement of the patient Referring to FIG. 9, assume that at time t, a first detector determines the patient's location to be $(S_m, q_m)$ relative to the first detector; and a second detector determines the patients location to be $(T'_m, r'_m)$ relative to the second detector.

Assuming that the distance between the two detectors is known and that the detectors are mounted in fixed positions then the patient's location is easily determined by using linear algebra. Of course, these polar coordinates values can easily be converted to Cartesian coordinates if desired.

Using triangulation, the patient's location can be known to a high degree of accuracy. In addition, the patient's rate of movement and direction of movement can easily be determined as well. For example, if we know that at time t the patient is at location L and that at time t' the patient is at location L', it is trivial to deduce the patient's speed and direction of movement The patient's movements thus determined may provide many valuable clues about the patient's state of mind. Patterns of behaviour and the incidents in which they are involved reflect critical variables and characteristics such as mood, heightened apprehension or overt panic, as well as periods of calm and relaxation. For example, rapid movement by an afflicted patient signifies a probable state of agitation. An increased heart rate would confirm a state of agitation.

Medical Organizer

Figure 4:
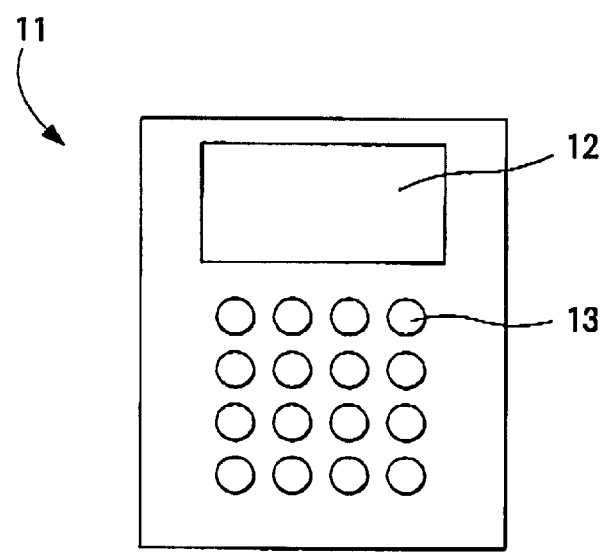
FIG. 4 illustrates an embodiment of a receiver/medical organizer of the present invention.

The information processed and compiled by the controller is sent wirelessly to a medical organizer. This medical organizer is a computerized device used by the caregiver to interface with the monitoring system. A suitably configured general purpose computer could be used, but it is preferred that, as shown in FIG. 4, the medical organizer be a compact handheld unit 11 with a screen 12 and control buttons 13 similar to a personal digital assistant (PDA) which is carried by the caregiver.

The information processed and compiled by the controller can be sent continually to the medical organizer thus providing a complete record of the patient's location, movements, heart rate and other information.

There is, however, another important aspect of the invention relating to event (incident) driven signals sent to the medical organizer. An incident occurs when the patient is too close to a hazard or a monitored location. More specifically, an incident occurs when the distance between the transmitter and the detector at the location of a hazard to be monitored falls below a predetermined threshold.

Upon determining that an incident has occurred, the controller transmits information to the medical organizer to record the incident. In addition to the information discussed above, the controller also transmits a signal to activate an alarm to alert the caregiver of the occurrence of an incident.

Upon receipt of a signal indicating the occurrence of an incident, the medical organizer records the details of the incident and alerts the caregiver. The means of alerting the caregiver can be any conventional means including an audio alarm or signal; a visual signal; or activating a pager carried by the caregiver. The medical organizer is also provided with a display screen to display information about the incident such as time of day; location of incident; nature of incident etc.

Upon being alerted, the caregiver can learn about the situation by consulting the display screen and can take suitable action. Since the detector is activated before the patient has reached the hazard or location in question, the caregiver is given advanced warning and thus has an opportunity to intervene by approaching the location of the event and trying to prevent the occurrence of an accident, injury or elopement. For example, if the patient approaches the front door of the house to leave, the caregiver is alerted while the patient is still in the house so that the caregiver can intercept the patient.

Following resolution of the incident, the caregiver is systematically guided by prompts on screen to enter critical observations relating to the incident. On-screen features also provide fields in which the caregiver can enter personal observations and can comment on the incident. This aspect of the system thus captures valuable observations made by caregivers and helps them to perceive themselves as a critical part of treatment.

An important feature of the system is that when a detector is located at a hazard such as an appliance, vehicle or other machine, the detector may be connected to a circuit breaker which will disable operation of the machine when the patient gets too close to the machine. The system is designed so that the patient is able to move as freely as possible and it may not be necessary to severely restrict patient's movement since certain hazardous situations can be detected and the hazard neutralized by the system or caregiver before harm can come to the patient.

EXAMPLES

The following examples are provided for purposes of illustration of the inventive concepts, and are not intended to limit the scope of the invention as defined by the appended claims 1. Automobile Disabling System As a specific example, an automobile accessible to the patient or other person requiring care may be provided with a detector. The detector could be a basic proximity detector but is preferably one which is configured so that it only detects the presence of the patient in the driver's seat. Thus, shielding could be provided so that a patient could sit in a passenger seat without activating the detector, thus enabling the patient to ride as a passenger without disabling the vehicle.

The detector and a corresponding controller could be connected to the automobile so these units are only activated upon starting the ignition of the automobile. This is to conserve energy and avoid draining power from the automobile, particularly, the automobile's battery. However, once the ignition is started, the detector is immediately actuated. It then operates to detect any suitable transmission within its intended field of coverage. Upon determination of the presence of the patient, i.e. the patient is in the vicinity of the driver's seat, the controller associated with the detector opens a circuit breaker and disables the ignition of the vehicle. Preferably the circuit breaker is configured to prevent power to the final phase of ignition, thus allowing the patient to operate, for example, the vehicle's entertainment system without allowing the patent to drive the vehicle.

2. Central Database via Internet

The information relating to the patient's location, movement, incidents, etc. received by the medical organizer is, in turn, transferred to a central database. Although this transfer could be accomplished in numerous ways, according to the present embodiment, the receiving unit transmits this information wirelessly via the internet on a routine basis to the central database.

The central database is designed to receive data transmitted via the internet by recognized sources such as institutions, patients or caregivers who have registered with the administrators of the central database and an associated website.

Accordingly, when a number of sources, each provided with a configuration of transmitters, detectors and receiving units for the detection and recording of incidents, contribute to the central database, the information accumulated in the central database becomes potentially more and more important for understanding, treating and possibly preventing dementia related disorders.

The information in the central database is accessible for retrieval via internet or other means, such as wireless means, by authorized users such as medical researchers and treating physicians. For example, the database may be available for ad hoc queries to authorized persons when they visit a website dedicated to research on Alzheimer's disease or related dementia. For more intensive analysis, it may be suitable to arrange direct access to the central database. For example a treating physician can access the central database to see data relating to a patient's progress as tracked by the system in the patient's supervised environment.

3. Monitoring of More Than One Patient

The system operates analogously to the above described system for a single patient, except that a plurality of patients are monitored by a single system. This may be the case, for example, in a hospital or other institutional setting.

Figure 3:
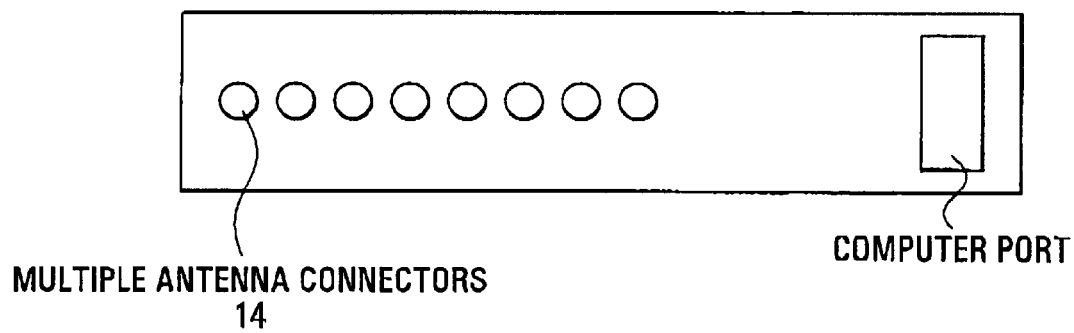
FIG. 3 illustrates an embodiment of a receiver/controller/transmitter unit of the present invention.

In order to implement a multi-patient system, part of which is shown diagrammatically in FIG. 3, a number of different transmission frequencies are used. The transmitter of each patient transmits using a different radio frequency. The antennae 14 of the detectors are capable of detecting all different frequencies but does so only one at a time. The software controlling each detector operates to ensure that the detector scans the different frequencies in turn and with sufficient rapidity that all patients are adequately tracked. This would not be difficult since the detector and controller are able to operate at speeds much faster than patients can move and the information about the position of each patient could, if desired, be refreshed several times each second. The refresh frequency (i.e. how many times the detector passes through, or scans, the zone) for monitoring movement may be determined according to the patients medical condition and could, for example be different for a person suffering from Alzheimer's compared to an autistic child. In other words, a suitable refreshment rate depends on the type of disorder being monitored as well as the age, agility and physical condition of the patient being monitored.

Software in the controller would be used to separately record the information received from each patient and track the movement, position and other information, as discussed above, for that patient The controller could also use the patient's identifier to confirm that the identity of the patient corresponds with the radio frequency assigned to that patient thereby preventing any possible confusion of data.

Figure 6:
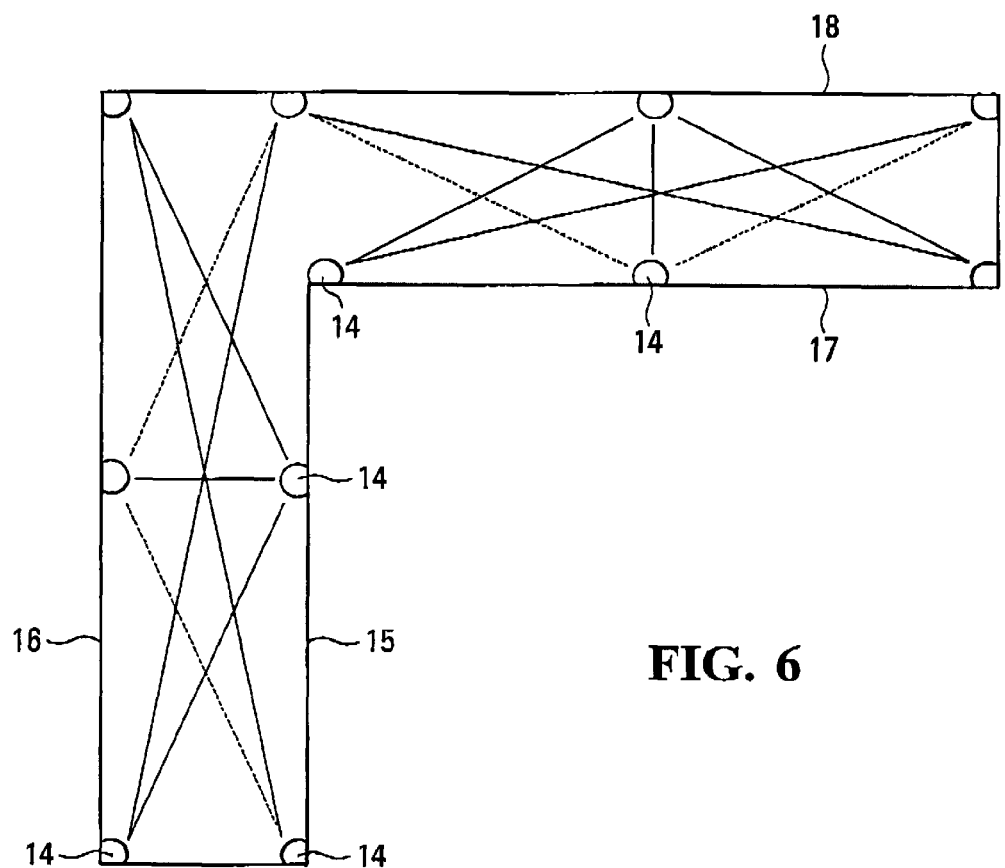
FIG. 6 illustrates diagrammatically the placement of detector receiving antennae along a hallway.
Figure 7:
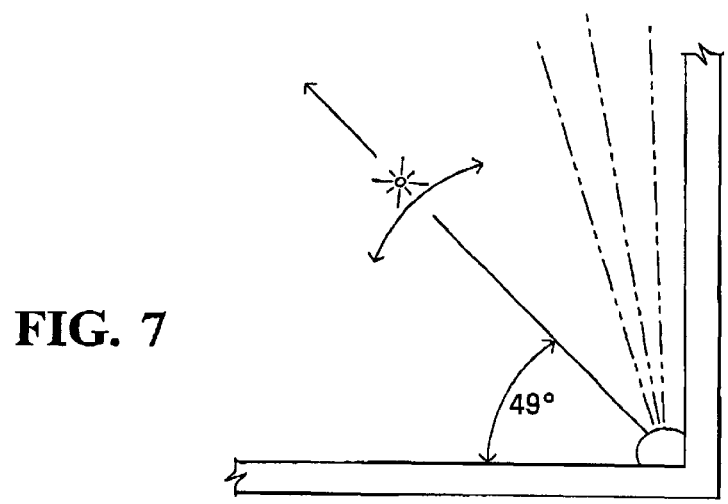
FIG. 7 illustrates an antenna having rotational capability.

The speed of rotation of the antennae and the radio frequency that is being used are controlled by the software portion of the system. The receiver transmits to the software the following information: who is in the area, time of contact and measurements of where the phase error disappears (angle of rotation). It is from these numerical measurements that the movements of the receivers can be computed. Because the antennae 14 are mounted in fixed positions on walls 15, 16, 17 and 18 (see FIG. 6), the distances between antennae remain constant. The first measurement for the equation for triangulation is the length of one side. The next measurement comes from the angle of rotation of the antenna (e.g. phase error disappears at 47 degrees). This gives the second measurement for triangulation, as the antennae move in sequential order. More angles of rotation are fed through the software allowing for the triangulation equation to be computed for movement.

4. Patient Monitoring System

This example of the system uses the same transmission portion. Where it varies is in the way it detects and calculates the position/location of the wearer of the transmitter.

This embodiment of the system uses phase error in determining the position of the transmitter. The detection system is a motor-mounted switched array antenna that measures phase error to determine the location of the transmission.

A bow tie array or similar antenna (also collects identification data) rotates at a given speed. The antenna is connected to the receiver through a diode-switching network. What occurs at this point is that an oscillator switches between the two wings of the antenna at about 1 KHz. When one wing of the antenna is slightly farther from the transmitter than the other, there is a phase error between the two received signals. This phase error disappears when the antenna wings are the same distance from the transmitter. At this given point the antenna array is at right angles to the direction of the transmitter.

The antennae are mounted at fixed positions on the walls, each systematically positioned for maximum triangulation effect. As the antennae rotate they do so at varying rates of speed for maximum triangulation effect. All the above mentioned calculations will be determined on individual basis, depending on location, room size, number of patients, etc.

As the antennae rotates, the angle of rotation is measured, as well they begin to measure phase error. When the phase error disappears on one antenna, that constitutes a first measurement for the angle of rotation for calculating movement. As the other antennae pass through the field of detection more measurements for triangulation are acquired. As the individual under surveillance moves, the transmitter moves with them thus creating a movement pattern into readable electronic data. The receiver remains the same and only transfers one additional piece of information, the angle where the phase error disappeared. This establishes the triangulation points.

I claim:

1. A system for monitoring a person under care, comprising:

a transmitter to be worn by the person and for emitting a signal including an identification corresponding to the person;

a detector being capable of detecting the signal and being capable of measuring different values of a physical parameter of the signal which provides different values of distance from the detector to the person as the distance varies, and being capable of transmitting the identification and transmitting information indicative of said different values of distance;

a controller for receiving from the detector, the identification and the information indicative of said different values of distance; and database means for storing information received by the controller from said detector.

2. The system of claim 1 wherein said detector is placed at or near a hazard, and wherein the occurrence of the value of distance from said detector to said person falling below a predetermined threshold indicates that an incident has occurred with respect to the person, and said detector is responsive to the occurrence of said incident to transmit information about said incident, and the controller is adapted to receive said information about said incident.

3. The system of claim 2 wherein the transmitter to be worn by the person is a radio frequency identification device.

4. The system of claim 3 wherein the transmitter to be worn by the person is housed within an electronic monitoring tag.

5. The system of claim 2 further including a medical organizer having a display screen, and wherein the controller is adapted to transmit said information about said incident to the medical organizer for display in the event that the controller receives said information about said incident.

6. The system of claim 5 further including a medical organizer to which the controller transmits information corresponding to the person, and wherein the medical organizer is capable of receiving observations and comments from a caregiver monitoring said person.

7. The system of claim 2 further including a medical organizer to which the controller transmits information corresponding to the person, and wherein the medical organizer is capable of receiving observations and comments from a caregiver monitoring said person.

8. The system of claim 2 wherein the detector is adapted such that if one of the different values of distance from the detector to the person falls below the predetermined threshold, the detector detects the occurrence of said incident.

9. The system of claim 8 wherein the detector is capable of deactivating the hazard in the event that the detector detects the occurrence of said incident.

10. The system of claim 9 further including an alarm, and wherein the detector is adapted to transmit a signal to the alarm in the event that the detector detects the occurrence of said incident.

11. The system of claim 8 further including an alarm, and wherein the detector is adapted to transmit a signal to the alarm in the event that the detector detects the occurrence of said incident.

12. The system of claim 11 further including a medical organizer having a display screen, and wherein the controller is adapted to transmit said information about said incident to the medical organizer for display in the event that the controller receives said information about said incident.

13. The system of claim 11 further including a medical organizer to which the controller transmits information corresponding to the person, and wherein the medical organizer is capable of receiving observations and comments from a caregiver monitoring said person.

14. The system of claim 1 wherein the transmitter to be worn by the person is a radio frequency identification device.

15. The system of claim 14 wherein the transmitter to be worn by the person is housed within an electronic monitoring tag.

16. The system of claim 1 further including a medical organizer to which the controller transmits information corresponding to the person, and wherein the medical organizer is capable of receiving observations and comments from a caregiver monitoring said person.

17. A system as claimed in claim 1, comprising one or more further detectors, each further detector being capable of detecting said signal and being capable of measuring different values of a physical parameter of the signal which provides different values of distance from the detector to the person as the distance varies, and being capable of transmitting the identification and transmitting information indicative of said different values of distance, said controller being adapted to receive from each further detector the identification and said information indicative of said different values of distance, and said database means being adapted to store information received by the controller from each further detector.

18. A system for monitoring a plurality of persons under care, comprising:

for each person, a transmitter to be worn by the person and for emitting a signal including an identification corresponding to the person;

a plurality of detectors, for each signal, each detector being capable of detecting the signal and being capable of measuring different values of a physical parameter of the signal which provides different values of distance from the detector to the person that corresponds to the signal as the distance varies, and being capable of transmitting the identification corresponding to the person included in the signal and transmitting information indicative of said different values of distance;

a plurality of receiving units, each receiving unit being capable of receiving from a detector the identification corresponding to each person and the information indicative of said different values of distance from said detector to each person, each receiving unit being capable of transmitting the identification corresponding to each person and transmitting the information indicative of said different values of distance from said detector to each person; and a central database remote from each receiving unit for storing information received by each receiving unit from said detector.

19. The system of claim 18 wherein the central database is accessible by means of the Internet.

20. The system of claim 18 wherein a detector of the plurality of detectors is placed at or near a hazard, and wherein the occurrence of the value of distance from said detector to a person corresponding to a signal falling below a predetermined threshold indicates that an incident has occurred with respect to said person, and said detector is responsive to the occurrence of said incident to transmit information about said incident, and a receiving unit capable of receiving information from said detector is adapted to receive said information about said incident and to transmit said information about said incident.

21. The system of claim 20 wherein the transmitter to be worn by each person is a radio frequency identification device.

22. The system of claim 21 wherein the transmitter to be worn by each person is housed within an electronic monitoring tag.

23. The system of claim 20 wherein the detector is adapted such that if one of the different values of distance from the detector to the person corresponding to the signal falls below the predetermined threshold, the detector detects the occurrence of said incident.

24. The system of claim 23 wherein the different values of the physical parameter of the signal are different values of strength of reception of the signal, and wherein the detector is adapted such that if one of the different values of strength of reception of the signal rises above a predetermined strength of reception threshold value the detector detects the occurrence of said incident by detecting that one of the different values of strength of reception of the signal has risen above the predetermined strength of reception threshold value.

25. The system of claim 18 wherein the transmitter to be worn by each person is a radio frequency identification device.

26. The system of claim 25 wherein the transmitter to be worn by each person is housed within an electronic monitoring tag.

27. A system for monitoring a plurality of persons under care, comprising:

for each person, a transmitter to be worn by the person and for emitting a signal including an identification corresponding to the person;

a detector, which for each signal, is capable of detecting the signal and is capable of measuring different values of a physical parameter of the signal which provides different values of distance from the detector to the person corresponding to the signal as the distance varies, and being capable of transmitting the identification corresponding to the person included in the signal and transmitting information indicative of said different values of distance;

a controller for receiving from the detector the identification corresponding to each person and the information indicative of said different values of distance from the detector to each person; and database means for storing information received by the controller from the detector.

28. The system of claim 27 wherein the detector is placed at or near a hazard, and wherein the occurrence of the value of distance from said detector to a person corresponding to a signal falling below a predetermined threshold indicates that an incident has occurred with respect to said person, and said detector is responsive to the occurrence of said incident to transmit information about said incident, and the controller receives the information about said incident.

29. The system of claim 28 wherein the detector is adapted such that if one of the different values of distance from the detector to the person corresponding to the signal fills below a predetermined threshold, the detector detects the occurrence of said incident.

30. The system of claim 29 wherein the detector is capable of deactivating the hazard in the event that the detector detects the occurrence of said incident.

31. The system of claim 30 further including an alarm, and wherein the detector is adapted to transmit a signal to the alarm in the event that the detector detects the occurrence of said incident.

32. The system of claim 29 further including an alarm, and wherein the detector is adapted to transmit a signal to the alarm in the event that the detector detects the occurrence of said incident.

33. The system of claim 32 further including a medical organizer having a display screen, and wherein the controller is adapted to transmit said information about said incident to the medical organizer for display in the event that the controller receives said information about said incident.

34. The system of claim 32 further including a medical organizer to which the controller transmits information corresponding to each person, and wherein the medical organizer is capable of receiving observations and comments from a caregiver monitoring a person of the plurality of persons.

35. The system of claim 28 wherein the transmitter to be worn by each person is a radio frequency identification device.

36. The system of claim 35 wherein the transmitter to be worn by each person is housed within an electronic monitoring tag.

37. The system of claim 28 further including a medical organizer having a display screen, and wherein the controller is adapted to transmit said information about said incident to the medical organizer for display in the event that the controller receives said information about said incident.

38. The system of claim 37 further including a medical organizer to which the controller transmits information corresponding to each person, and wherein the medical organizer is capable of receiving observations and comments from a caregiver monitoring a person of the plurality of persons.

39. The system of claim 28 further including a medical organizer to which the controller transmits information corresponding to each person, and wherein the medical organizer is capable of receiving observations and comments from a caregiver monitoring a person of the plurality of persons.

40. The system of claim 27 wherein the transmitter to be worn by each person is a radio frequency identification device.

41. The system of claim 40 wherein the transmitter to be worn by each person is housed within an electronic monitoring tag.

42. The system of claim 27 further including a medical organizer to which the controller transmits information corresponding to each person, and wherein the medical organizer is capable of receiving observations and comments from a caregiver monitoring a person of the plurality of persons.

43. A system as claimed in claim 27, comprising one or more further detectors, for each signal, each further detector being capable of detecting the signal and being capable of measuring different values of a physical parameter of the signal which provides different values of distance from the detector to the person corresponding to the signal as the distance varies, and being capable of transmitting the identification corresponding to the person included in the signal and transmitting information indicative of said different values of distance, for each signal, said controller being adapted to receive from each further detector the identification corresponding to the person included in the signal and said information indicative of said different values of distance, and said database means being adapted to store information received by the controller from each further detector.

* * * * *

UNITED STATES PATENT AND TRADEMARK OFFICE
CERTIFICATE OF CORRECTION

PATENT NO.    : 6,753,782 B2  
DATED         : June 22, 2004  
INVENTOR(S)   : Michael W. Power It is certified that error appears in the above-identified patent and that said Letters Patent is hereby corrected as shown below:

<u>Title page,</u>  
Item [30], Foreign Application Priority Data, "Jan. 11, 2000" should be -- November 1, 2000 --.

<u>Column 13,</u>  
Line 25, "...fills..." should be -- ...falls... --.

Signed and Sealed this

Thirteenth Day of December, 2005

JON W. DUDAS  
*Director of the United States Patent and Trademark Office*